(12) United States Patent
Wang et al.

(10) Patent No.: US 9,011,656 B2
(45) Date of Patent: *Apr. 21, 2015

(54) SMALL VOLUME TEST STRIPS WITH LARGE SAMPLE FILL PORTS, SUPPORTED TEST STRIPS, AND METHODS OF MAKING AND USING SAME

(71) Applicant: Abbott Diabetes Care Inc., Alameda, CA (US)

(72) Inventors: Yi Wang, San Ramon, CA (US); Shridhara Alva Karinka, Pleasanton, CA (US); Benjamin J. Feldman, Berkeley, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/219,298

(22) Filed: Mar. 19, 2014

(65) Prior Publication Data

US 2014/0202853 A1  Jul. 24, 2014

Related U.S. Application Data

(63) Continuation of application No. 13/738,585, filed on Jan. 10, 2013, now Pat. No. 8,679,311, which is a continuation of application No. 12/551,316, filed on Aug. 31, 2009, now Pat. No. 8,357,276.

(51) Int. Cl.
*G01N 27/327* (2006.01)
*B32B 37/14* (2006.01)

(52) U.S. Cl.
CPC ............... *G01N 27/327* (2013.01); *B32B 37/14* (2013.01); *G01N 27/3272* (2013.01)

(58) Field of Classification Search
CPC ............... G01N 27/327–27/3274; B32B 37/14
USPC ............ 204/409, 403.01–403.15; 422/82.01; 435/4, 14, 25–28
See application file for complete search history.

(56) References Cited

U.S. PATENT DOCUMENTS

| | | |
|---|---|---|
| 4,545,382 A | 10/1985 | Higgins et al. |
| 4,711,245 A | 12/1987 | Higgins et al. |
| 5,262,035 A | 11/1993 | Gregg et al. |
| 5,262,305 A | 11/1993 | Heller et al. |
| 5,264,104 A | 11/1993 | Gregg et al. |
| 5,320,725 A | 6/1994 | Gregg et al. |
| 5,356,786 A | 10/1994 | Heller et al. |
| 5,509,410 A | 4/1996 | Hill et al. |
| 5,547,702 A | 8/1996 | Gleisner |
| 5,593,852 A | 1/1997 | Heller et al. |
| 5,601,435 A | 2/1997 | Quy |
| 5,628,890 A | 5/1997 | Carter et al. |
| 5,820,551 A | 10/1998 | Hill et al. |
| 5,822,715 A | 10/1998 | Worthington et al. |
| 5,851,838 A | 12/1998 | Vetter et al. |

(Continued)

FOREIGN PATENT DOCUMENTS

WO    WO 2008/040997 A1 * 4/2008

*Primary Examiner* — J. Christopher Ball
(74) *Attorney, Agent, or Firm* — Edward J. Baba; Shweta Chandra; Bozicevic, Field & Francis LLP

(57) ABSTRACT

The present disclosure provides small volume analyte sensors having large sample fill ports, supported analyte sensors, analyte sensors having supported tip protrusions and methods of making and using same.

20 Claims, 9 Drawing Sheets

(56) References Cited

U.S. PATENT DOCUMENTS

| | | |
|---|---|---|
| 5,899,855 A | 5/1999 | Brown |
| 5,918,603 A | 7/1999 | Brown |
| 6,071,391 A | 6/2000 | Gotoh et al. |
| 6,120,676 A | 9/2000 | Heller et al. |
| 6,121,009 A | 9/2000 | Heller et al. |
| 6,143,164 A | 11/2000 | Heller et al. |
| 6,144,837 A | 11/2000 | Quy |
| 6,161,095 A | 12/2000 | Brown |
| 6,175,752 B1 | 1/2001 | Say et al. |
| 6,270,455 B1 | 8/2001 | Brown |
| 6,281,006 B1 | 8/2001 | Heller et al. |
| 6,284,478 B1 | 9/2001 | Heller |
| 6,299,757 B1 | 10/2001 | Feldman et al. |
| 6,338,790 B1 | 1/2002 | Feldman et al. |
| 6,377,894 B1 | 4/2002 | Deweese et al. |
| 6,461,496 B1 | 10/2002 | Feldman et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,560,471 B1 | 5/2003 | Heller et al. |
| 6,591,125 B1 | 7/2003 | Buse et al. |
| 6,592,745 B1 | 7/2003 | Feldman et al. |
| 6,600,997 B2 | 7/2003 | Deweese et al. |
| 6,616,819 B1 | 9/2003 | Liamos et al. |
| 6,618,934 B1 | 9/2003 | Feldman et al. |
| 6,638,716 B2 | 10/2003 | Heller et al. |
| 6,676,816 B2 | 1/2004 | Mao et al. |
| 6,730,200 B1 | 5/2004 | Stewart et al. |
| 6,736,957 B1 | 5/2004 | Forrow et al. |
| 6,746,582 B2 | 6/2004 | Heller et al. |
| 6,749,740 B2 | 6/2004 | Liamos et al. |
| 6,764,581 B1 | 7/2004 | Forrow et al. |
| 6,773,671 B1 | 8/2004 | Lewis et al. |
| 6,881,551 B2 | 4/2005 | Heller et al. |
| 6,893,545 B2 | 5/2005 | Gotoh et al. |
| 6,942,518 B2 | 9/2005 | Liamos et al. |
| 7,041,468 B2 | 5/2006 | Drucker et al. |
| 7,122,110 B2 | 10/2006 | Deng et al. |
| 7,144,485 B2 | 12/2006 | Hsu et al. |
| 7,167,818 B2 | 1/2007 | Brown |
| 7,225,535 B2 | 6/2007 | Feldman et al. |
| 7,299,082 B2 | 11/2007 | Feldman et al. |
| 7,501,053 B2 | 3/2009 | Karinka et al. |
| 7,550,069 B2 | 6/2009 | Feldman et al. |
| 7,563,350 B2 | 7/2009 | Feldman et al. |
| D611,854 S | 3/2010 | Wang et al. |
| 8,357,276 B2 * | 1/2013 | Wang et al. ............... 204/403.14 |
| 2004/0186365 A1 | 9/2004 | Jin et al. |
| 2005/0008537 A1 | 1/2005 | Mosoiu et al. |
| 2006/0025662 A1 | 2/2006 | Buse et al. |
| 2006/0091006 A1 | 5/2006 | Wang et al. |
| 2006/0169599 A1 | 8/2006 | Feldman et al. |
| 2006/0292650 A1 | 12/2006 | Braig et al. |
| 2007/0068807 A1 | 3/2007 | Feldman et al. |
| 2007/0095661 A1 | 5/2007 | Wang et al. |
| 2007/0108048 A1 | 5/2007 | Wang et al. |
| 2007/0193019 A1 | 8/2007 | Feldman et al. |
| 2007/0199818 A1 | 8/2007 | Petyt et al. |
| 2008/0060196 A1 | 3/2008 | Wang et al. |
| 2008/0066305 A1 | 3/2008 | Wang et al. |
| 2008/0102441 A1 | 5/2008 | Chen et al. |
| 2008/0148873 A1 * | 6/2008 | Wang ........................ 73/864.73 |
| 2008/0267823 A1 | 10/2008 | Wang et al. |
| 2009/0011449 A1 | 1/2009 | Karinka et al. |
| 2009/0014328 A1 | 1/2009 | Feldman et al. |
| 2009/0060789 A1 | 3/2009 | Aas et al. |
| 2009/0095625 A1 | 4/2009 | Forrow |
| 2009/0211344 A1 | 8/2009 | Wang |
| 2009/0215159 A1 | 8/2009 | Kirby |
| 2009/0255811 A1 | 10/2009 | Forrow et al. |

* cited by examiner

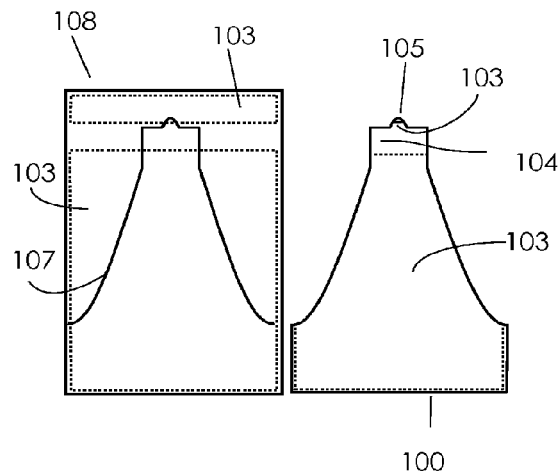
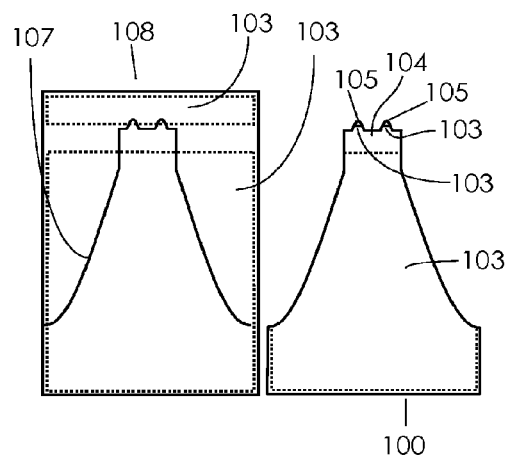
FIG. 9A  FIG. 9B
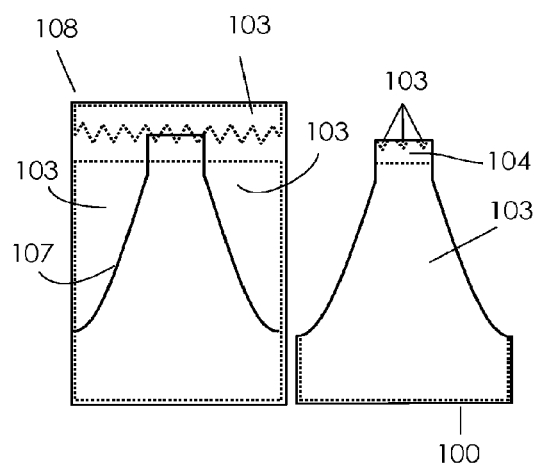
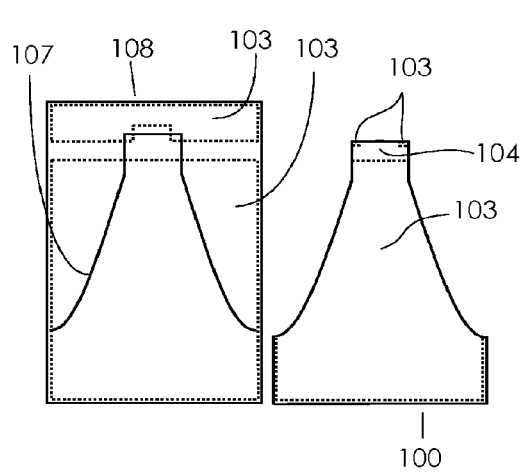
FIG. 9C  FIG. 9D

SMALL VOLUME TEST STRIPS WITH LARGE SAMPLE FILL PORTS, SUPPORTED TEST STRIPS, AND METHODS OF MAKING AND USING SAME

BACKGROUND OF THE INVENTION

Analytical sensors are commonly used to determine the presence and/or concentration of an analyte in a biological sample. Such sensors are used, for example, to monitor blood glucose levels in diabetic patients. For many applications, it may be desirable to utilize as small a sample as practicable to perform a particular analysis. As such, there is interest in the art in obtaining analyte sensors, e.g., test strips, which include features that facilitate the loading of relatively small sample volumes.

SUMMARY OF THE INVENTION

The present disclosure provides small volume analyte sensors having large sample fill ports, supported analyte sensors, analyte sensors having supported tip protrusions. Methods of making and using the disclosed analyte sensors are also provided. These and other objects, features and advantages of the present disclosure will become more fully apparent from the following detailed description of the embodiments, the appended claims and the accompanying drawings.

In a first aspect, the present disclosure provides an analyte sensor which includes a sample chamber, the sample chamber including a sample fill port, wherein the sample chamber has a volume ($V_c$) in $mm^3$, the sample fill port has an area ($A_p$) in $mm^2$ and $A_p/V_c$ is greater than 0.75 1/mm.

In one embodiment of the first aspect, $A_p/V_c$ is greater than 1.0 1/mm.

In another embodiment of the first aspect, $A_p/V_c$ is greater than 1.5 1/mm.

In another embodiment of the first aspect, $A_p/V_c$ is greater than 2.0 1/mm.

In another embodiment of the first aspect, $A_p/V_c$ is greater than 2.5 1/mm.

In another embodiment of the first aspect, $A_p/V_c$ is greater than 3.0 1/mm.

In another embodiment of the first aspect, $V_c$ is less than 0.10 $mm^3$.

In another embodiment of the first aspect, $V_c$ is less than 0.075 $mm^3$.

In another embodiment of the first aspect, $V_c$ is less than 0.050 $mm^3$.

In another embodiment of the first aspect, the analyte sensor includes a plurality of electrodes. In one such embodiment, one of the plurality of electrodes includes an analyte-responsive enzyme. In one embodiment, the analyte-responsive enzyme is a glucose-responsive enzyme or a ketone-responsive enzyme.

In a second aspect, the present disclosure provides an analyte sensor as described in the first aspect, wherein the analyte sensor includes: a first substrate having a proximal end and a distal end; a second substrate having a proximal end and a distal end; a plurality of spacers positioned between the first substrate and the second substrate, wherein the plurality of spacers are positioned in a single plane, wherein the first substrate, the second substrate, and the plurality of spacers together define the sample chamber, the sample chamber including a perimeter including a bounded region defined by defined by the plurality of spacers and an unbounded region open to the external environment, and wherein the unbounded region is greater in distance than the bounded region.

In one embodiment of the second aspect, the plurality of spacers includes at least three spacers. In one such embodiment, two of the at least three spacers are positioned between the proximal end of the first substrate and the proximal end of the second substrate.

In another embodiment of the second aspect, the plurality of spacers includes at least four spacers. In one such embodiment, three of the at least four spacers are positioned between the proximal end of the first substrate and the proximal end of the second substrate.

In another embodiment of the second aspect, the plurality of spacers includes at least five spacers. In one such embodiment, the at least five spacers are positioned between the proximal end of the first substrate and the proximal end of the second substrate.

In another embodiment of the second aspect, the first substrate includes a first protrusion positioned at the proximal end of the first substrate, the second substrate includes a second protrusion positioned at the proximal end of the second substrate, and one of the plurality of spacers is positioned between the first protrusion and the second protrusion. In one such embodiment, the first substrate includes a third protrusion positioned at the proximal end of the first substrate, the second substrate includes a fourth protrusion positioned at the proximal end of the second substrate and one of the plurality of spacers is positioned between the third protrusion and the fourth protrusion.

In another embodiment of the second aspect, each of the plurality of spacers is an adhesive material.

In another embodiment of the second aspect, the analyte sensor includes a plurality of electrodes. In one such embodiment, one of the plurality of electrodes includes an analyte-responsive enzyme. In one embodiment, the analyte-responsive enzyme is a glucose-responsive enzyme or a ketone-responsive enzyme.

In a third aspect, the present disclosure provides an analyte sensor which includes: a first substrate having a proximal end and a distal end; a second substrate having a proximal end and a distal end; a first protrusion positioned at the proximal end of the first substrate; a second protrusion positioned at the proximal end of the second substrate; a plurality of spacers positioned between the first substrate and the second substrate; wherein the plurality of spacers is positioned in a single plane; the first substrate, the second substrate, and the plurality of spacers together define a sample chamber; and a spacer of the plurality of spacers is positioned between the first protrusion and the second protrusion.

In one embodiment of the third aspect, the spacer positioned between the first protrusion and the second protrusion is positioned only between the first protrusion and the second protrusion.

In another embodiment of the third aspect, the sample chamber includes a perimeter, the perimeter including a bounded region defined by the plurality of spacers and an unbounded region open to the external environment, wherein the unbounded region is greater in length than the bounded region.

In another embodiment of the third aspect, the first substrate includes a third protrusion positioned at the proximal end of the first substrate, the second substrate includes a fourth protrusion positioned at the proximal end of the second substrate and another of the plurality of spacers is positioned between the third protrusion and the fourth protrusion.

In another embodiment of the third aspect, each of the plurality of spacers is an adhesive material.

In another embodiment of the third aspect, the analyte sensor includes a plurality of electrodes. In one such embodiment, one of the plurality of electrodes includes an analyte-responsive enzyme. In one embodiment, the analyte-responsive enzyme is a glucose-responsive enzyme or a ketone-responsive enzyme.

In a fourth aspect, the present disclosurer provides an analyte sensor as described in the third aspect, wherein the sample chamber includes a sample fill port, the sample chamber has a volume ($V_c$) in mm$^3$, the sample fill port has an area ($A_p$) in mm$^2$ and $A_p/V_c$ is greater than 0.75 1/mm.

In one embodiment of the fourth aspect, $A_p/V_c$ is greater than 1.0 1/mm.

In another embodiment of the fourth aspect, $A_p/V_c$ is greater than 1.5 1/mm.

In another embodiment of the fourth aspect, $A_p/V_c$ is greater than 2.0 1/mm.

In another embodiment of the fourth aspect, $A_p/V_c$ is greater than 2.5 1/mm.

In another embodiment of the fourth aspect, $A_p/V_c$ is greater than 3.0 1/mm.

In another embodiment of the fourth aspect, $V_c$ is less than 0.10 mm$^3$.

In another embodiment of the fourth aspect, $V_c$ is less than 0.075 mm$^3$.

In another embodiment of the fourth aspect, $V_c$ is less than 0.050 mm$^3$.

In a fifth aspect, the present disclosure provides an analyte sensor which includes: a first substrate having a proximal end and a distal end; a second substrate having a proximal end and a distal end; a plurality of spacers positioned between the first substrate and the second substrate; wherein the plurality of spacers is positioned in a single plane; the first substrate, the second substrate, and the plurality of spacers together define a sample chamber; and the plurality of spacers is positioned such that a plurality of sample fill areas are provided through which the sample chamber can be simultaneously filled with a sample.

In one embodiment of the fifth aspect, the sample chamber includes a perimeter, the perimeter including a bounded region defined by the plurality of spacers and an unbounded region open to the external environment, wherein the unbounded region is greater in length than the bounded region.

In another embodiment of the fifth aspect, each of the plurality of spacers is an adhesive material.

In another embodiment of the fifth aspect, the analyte sensor includes a plurality of electrodes. In one such embodiment, one of the plurality of electrodes includes an analyte-responsive enzyme. In one embodiment, the analyte-responsive enzyme is a glucose-responsive enzyme or a ketone-responsive enzyme.

In a sixth aspect, the present disclosure provides an analyte sensor as described in the fifth aspect, wherein the sample chamber includes a sample fill port, the sample chamber has a volume ($V_c$) in mm$^3$, the sample fill port has an area ($A_p$) in mm$^2$ and $A_p/V_c$ is greater than 0.75 1/mm.

In one embodiment of the sixth aspect, $A_p/V_c$ is greater than 1.0 1/mm.

In another embodiment of the sixth aspect, $A_p/V_c$ is greater than 1.5 1/mm.

In another embodiment of the sixth aspect, $A_p/V_c$ is greater than 2.0 1/mm.

In another embodiment of the sixth aspect, $A_p/V_c$ is greater than 2.5 1/mm.

In another embodiment of the sixth aspect, $A_p/V_c$ is greater than 3.0 1/mm.

In another embodiment of the sixth aspect, $V_c$ is less than 0.10 mm$^3$.

In another embodiment of the sixth aspect, $V_c$ is less than 0.075 mm$^3$.

In another embodiment of the sixth aspect, $V_c$ is less than 0.050 mm$^3$.

In a seventh aspect, the present disclosure provides a method of making an analyte sensor having supported protrusions, wherein the method includes: combining a first substrate having a proximal end and a distal end, a second substrate having a proximal end and a distal end, and a plurality of spacers to provide a layered structure having the plurality of spacers positioned in a plane between the first substrate and the second substrate. The method also includes removing material from the layered structure to provide an analyte sensor having a first protrusion at the proximal end of the first substrate and a second protrusion at the proximal end of the second substrate, wherein the first protrusion and the second protrusion are supported by one of the plurality of spacers, or a portion thereof, positioned between the first protrusion and the second protrusion.

In one embodiment of the seventh aspect, the removing further includes removing material from the layered structure to provide a third protrusion at the proximal end of the first substrate and a fourth protrusion at the proximal end of the second substrate, wherein the third protrusion and the fourth protrusion are supported by one of the plurality of spacers, or a portion thereof, positioned between the third protrusion and the fourth protrusion.

In another embodiment of the seventh aspect, the removing includes punching the layered structure to provide the analyte sensor.

In another embodiment of the seventh aspect, the removing includes cutting the layered structure to provide the analyte sensor.

In another embodiment of the seventh aspect, each of the plurality of spacers includes an adhesive material.

In another embodiment of the seventh aspect, the method further includes depositing the plurality of spacers on the first or second substrate as a single layer.

In an eighth aspect, the present disclosure provides a method as provided in the seventh aspect, wherein the analyte sensor includes a sample chamber, the sample chamber including a sample fill port, wherein the sample chamber has a volume ($V_c$) in mm$^3$, the sample fill port has an area ($A_p$) in mm$^2$ and $A_p/V_c$ is greater than 0.75 1/mm.

In one embodiment of the eighth aspect, $A_p/V_c$ is greater than 1.0 1/mm.

In another embodiment of the eighth aspect, $A_p/V_c$ is greater than 1.5 1/mm.

In another embodiment of the eighth aspect, $A_p/V_c$ is greater than 2.0 1/mm.

In another embodiment of the eighth aspect, $A_p/V_c$ is greater than 2.5 1/mm.

In another embodiment of the eighth aspect, $A_p/V_c$ is greater than 3.0 1/mm.

In another embodiment of the eighth aspect, $V_c$ is less than 0.10 mm$^3$.

In another embodiment of the eighth aspect, $V_c$ is less than 0.075 mm$^3$.

In another embodiment of the eighth aspect, $V_c$ is less than 0.050 mm$^3$.

In a ninth aspect, the present disclosure provides a method as described in the seventh aspect, wherein the plurality of spacers includes a spacer which includes an edge defining a repeating geometric pattern.

In one embodiment of the ninth aspect, the first protrusion and the second protrusion are supported by a portion of the spacer including an edge defining a repeating geometric pattern.

In another embodiment of the ninth aspect, the repeating geometric pattern is a sawtooth pattern, a wave pattern or a crenellation pattern.

In a tenth aspect, the present disclosure provides a method of making an analyte sensor having a plurality of proximal supports, the method including: combining a first substrate having a proximal end and a distal end, a second substrate having a proximal end and a distal end, and a plurality of spacers to provide a layered structure having the plurality of spacers positioned in a plane between the first substrate and the second substrate. The method also includes removing material from the layered structure to provide an analyte sensor having a first portion of one of the plurality of spacers positioned between the proximal end of the first substrate and the proximal end of the second substrate, and a second portion of the one of the plurality of spacers positioned between the proximal end of the first substrate and the proximal end of the second substrate, wherein the first and second portions of the one of the plurality of spacers are not in contact.

In one embodiment of the tenth aspect, the removing includes punching the layered structure to provide the analyte sensor.

In another embodiment of the tenth aspect, the removing includes cutting the layered structure to provide the analyte sensor.

In another embodiment of the tenth aspect, each of the plurality of spacers includes an adhesive material.

In another embodiment of the tenth aspect, the method further includes depositing the plurality of spacers on the first or second substrate as a single layer.

In another embodiment of the tenth aspect, the one of the plurality of spacers includes a spacer which includes an edge defining a repeating geometric pattern. In one such embodiment, the repeating geometric pattern is a sawtooth pattern, a wave pattern or a crenellation pattern.

In an eleventh aspect, the present disclosure provides a method as described in the tenth aspect, wherein the analyte sensor includes a sample chamber, the sample chamber including a sample fill port, the sample chamber has a volume ($V_c$) in mm$^3$, the sample fill port has an area ($A_p$) in mm$^2$ and $A_p/V_c$ is greater than 0.75 1/mm.

In one embodiment of the eleventh aspect, $A_p/V_c$ is greater than 1.0 1/mm.

In another embodiment of the eleventh aspect, $A_p/V_c$ is greater than 1.5 1/mm.

In another embodiment of the eleventh aspect, $A_p/V_c$ is greater than 2.0 1/mm.

In another embodiment of the eleventh aspect, $A_p/V_c$ is greater than 2.5 1/mm.

In another embodiment of the eleventh aspect, $A_p/V_c$ is greater than 3.0 1/mm.

In another embodiment of the eleventh aspect, $V_c$ is less than 0.10 mm$^3$.

In another embodiment of the eleventh aspect, $V_c$ is less than 0.075 mm$^3$.

In another embodiment of the eleventh aspect, $V_c$ is less than 0.050 mm$^3$.

BRIEF DESCRIPTION OF THE DRAWINGS

The invention is best understood from the following detailed description when read in conjunction with the accompanying drawings. It is emphasized that, according to common practice, the various features of the drawings are not necessarily to-scale. The dimensions of the various features are arbitrarily expanded or reduced for clarity. Included in the drawings are the following figures:

FIG. 3A shows individual components of the analyte prior to assembly; FIG. 3B shows a top view of an assembled version of the analyte sensor;

FIG. 5A shows individual components of the analyte prior to assembly; FIG. 5B shows a top view of an assembled version of the analyte sensor;

FIG. 7A shows individual components of the analyte prior to assembly; FIG. 7B shows a top view of an assembled version of the analyte sensor;

FIGS. 9A, 9B, 9C and 9D illustrate methods of making analyte sensors according to the present disclosure.

Figure 1A:
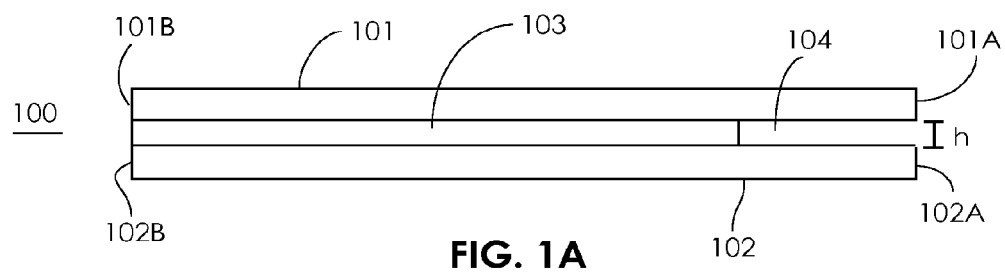
FIGS. 1A, 1B, 1C and 1D show a first side view (1A), a second side view (1B), a perspective view (1C) and a top view (1D) of an exemplary analyte sensor according to the present disclosure.
Figure 1B:
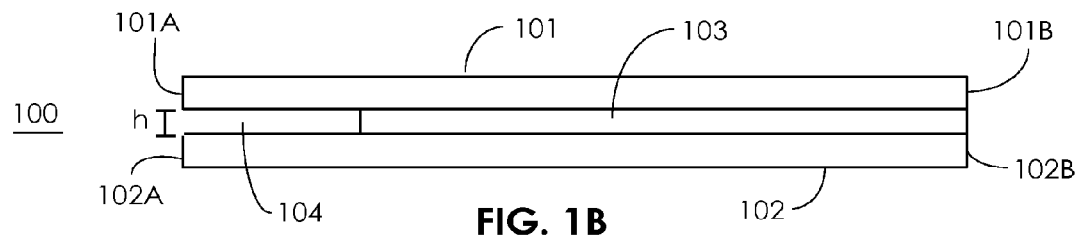

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein and in the appended claims, the singular forms "a," "and," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

As summarized above, the present disclosure is directed to small volume analyte sensors having large sample fill ports and analyte sensors having supported tip protrusions. Methods of making and using the disclosed analyte sensors are also provided.

Analyte Sensors

Disclosed herein are analyte sensors designed to detect and/or quantitate an analyte in a portion of a sample having a small volume, e.g., a volume of less than about 1 μL. For example, the analyte sensors can be designed to measure the concentration of an analyte in a portion of a sample having a volume less than about 100 nL, less than about 75 nL, or less than about 50 nL. The analyte of interest is typically provided in a solution or biological fluid, such as blood or serum.

With reference to FIGS. 1A-1D, an exemplary analyte sensor 100 is now described. Analyte sensor 100 includes a first substrate 101, a second substrate 102, one or more spacers 103, a working electrode (not shown), and a reference/counter electrode (not shown). Together, first substrate 101, second substrate 102 and the one or more spacers 103 define a sample chamber 104 between substrate 101 and substrate 102. A measurement zone (not shown) is present within the sample chamber. The measurement zone is configured such that when a sample is provided in the measurement zone the sample is in electrolytic contact with the working electrode and the reference/counter electrode (not shown).

Ratio of Fill Area to Volume of the Sample Chamber

In some embodiments, as described in greater detail below, analyte sensors according to the present disclosure have a relatively high sample port area to sample chamber volume ratio. As discussed above, one or more spacers 103, together with substrates 101 and 102, define the sample chamber 104. Sample chamber 104 can be described as having a volume ($V_c$) which is equal to the area of the sample chamber 104 ($A_c$)×the height (h) of sample chamber 104, i.e., $V_c=A_c \times h$. For example, with reference to FIGS. 1A-1D, the area of the sample chamber 104 ($A_c$) is equal to distance L1×distance L2. If one assumes, for illustration purposes, that L1 and L2 are each 1 mm and that h is 0.1 mm, then $V_c$ would be equal to 1 mm²×0.1 mm, which is equal to 0.1 mm³ (or 0.1 μL).

In some embodiments, e.g., as shown in FIGS. 2A-2D, an analyte sensor 100 may have a substrate 101 which is not coextensive with substrate 102, e.g., where the proximal end of substrate 101 extends beyond the proximal end of substrate 102 or vice versa. For the purposes of such embodiments, when calculating sample chamber volume ($V_c$) as described herein distances L1 and L2 are measured as shown in FIGS. 2A-2D, i.e., L1 and L2 extend to the proximal end of the shorter substrate (substrate 102 in FIGS. 2A-2D). In addition, the height (h) of the sample chamber 104, is measured as a perpendicular distance which extends from the inner surface of substrate 101 to the inner surface of substrate 102, e.g., as shown in FIGS. 2A-2D.

In addition, one or more spacers 103, together with substrates 101 and 102, define a sample fill port 106. As used herein, the term "sample fill port" refers to the total surface area of a sample chamber that is exposed to the external environment and through which liquid sample can access the sample chamber. The sample fill port 106 can be described as having a surface area ($A_p$) which is equal to the exposed region of the perimeter of sample chamber 104 ($L_p$)×the height (h) of the sample chamber 104, i.e., $A_p=L_p \times h$. For example, with reference to FIGS. 1A-1D, the exposed region of the perimeter of sample chamber 104 is equal to distance L1+distance L2+distance L3. If one assumes, for illustration purposes, that L1, L2 and L3 are each 1 mm, then $L_p$ would be equal to 3 mm. If one also assumes, for illustration purposes, that h is equal to 0.1 mm, then $A_p$ would be equal to 3 mm×0.1 mm, which is equal to 0.3 mm².

Figure 1C:
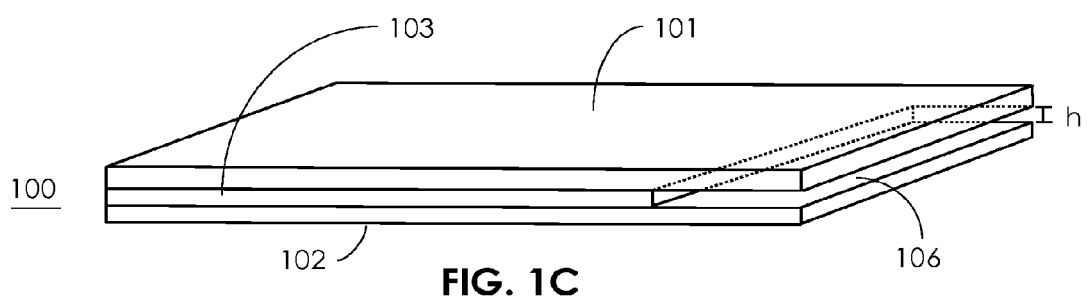
Figure 1D:
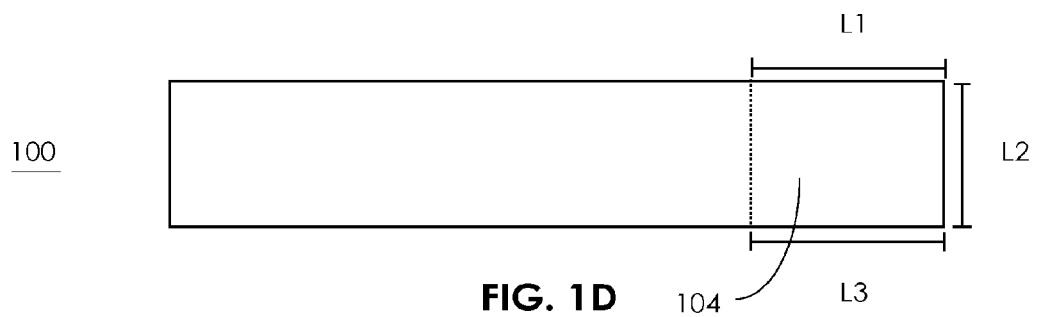
Figure 2A:
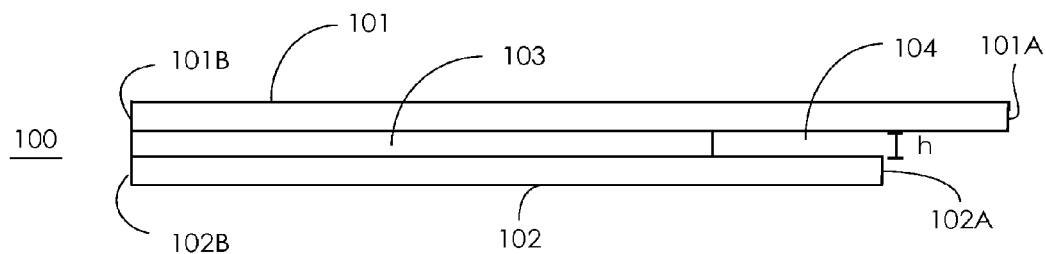
FIGS. 2A, 2B, 2C and 2D show a first side view (2A), a second side view (2B), a perspective view (2C) and a top view (2D) of another exemplary analyte sensor according to the present disclosure.
Figure 2B:
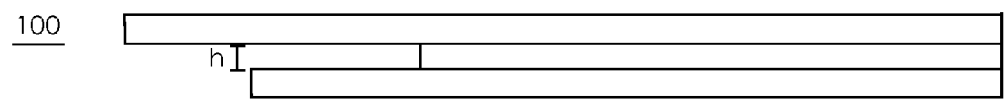
Figure 2C:
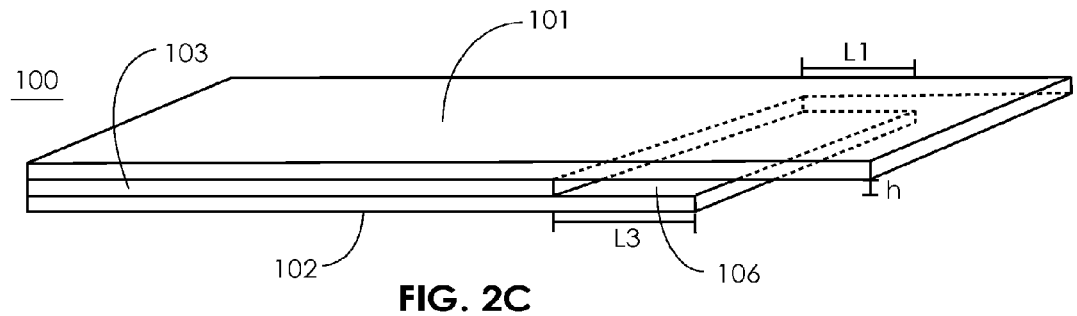
Figure 2D:
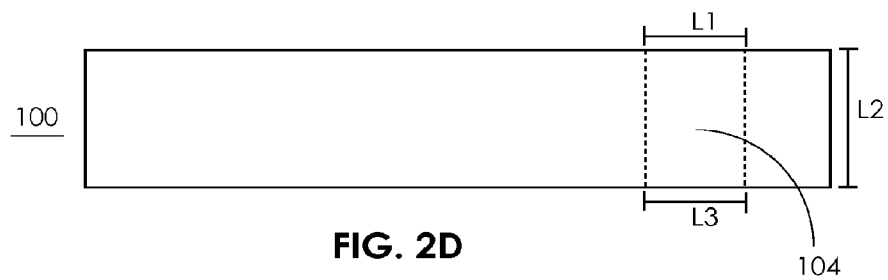

It should be noted that L1, L2, and L3 need not be contiguous as shown in FIG. 1C in order to calculate $L_p$. For example, with reference to FIG. 3B, the exposed region of the perimeter of sample chamber 104 ($L_p$) is equal to distance L1+distance L2+distance L3, where L1, L2 and L3 are not contiguous. Similarly, in the embodiment shown in FIG. 5B, where there are four exposed regions of the perimeter of sample chamber 104 and the four exposed regions are not contiguous, $L_p=L1+L2+L3+L4$.

In some embodiments, e.g., as shown in FIGS. 2A-2D, an analyte sensor 100 may have a substrate 101 which is not coextensive with substrate 102, e.g., where the proximal end of substrate 101 extends beyond the proximal end of substrate 102 or vice versa. For the purposes of such embodiments, when calculating sample fill port surface area ($A_p$) as described herein distances L1, L2 and L3 are measured as shown in FIGS. 2A-2D, i.e., L1 and L2 extend to the proximal end of the shorter substrate (substrate 102 in FIGS. 2A-2D). In addition, the height (h) of the sample chamber 104, is measured as a perpendicular distance which extends from the inner surface of substrate 101 to the inner surface of substrate 102, e.g., as shown in FIGS. 2A-2D.

By comparing the area of sample fill port 106 ($A_p$) with the volume of sample chamber 104 ($V_c$) for an analyte sensor 100, a surface area to volume ratio $A_p/V_c$ can be provided which characterizes the analyte sensor 100. Given the exemplary values above, this ratio would be equal to 0.3 mm²/0.1 mm³, which is equal to 3.0 1/mm. Furthermore, with the guidance provide herein and the exemplary calculations provided, one can readily calculate surface area to volume ratios for analyte sensors having any of a wide variety of configurations, e.g., analyte sensors having substrates with curved or angular proximal ends, so as to compare such ratios to those disclosed herein.

Where, as exemplified above, h is the same for calculation of both $A_p$ and $V_c$, the above ratio can be simplified to $L_p/A_c$. That is, the ratio of sample port area to sample chamber volume area is equivalent to the ratio of the exposed region of the perimeter of sample chamber 104 ($L_p$) to the area of the sample chamber 104 ($A_c$).

As discussed above, in some embodiments, analyte sensors according to the present disclosure include a sample chamber 104, where the sample chamber includes a sample fill port 106. In particular embodiments, sample chamber 104 has a volume ($V_c$) in mm³, sample fill port 106 has an area ($A_p$) in mm², and the ratio $A_p/V_c$ is greater than about 0.75 1/mm, e.g., greater than about 1.0 1/mm, greater than about 1.5 1/mm, greater than about 2.0 1/mm, greater than about 2.5

1/mm, or greater than about 3.0 1/mm. In some embodiments, the ratio $A_p/V_c$ is from about 0.75 1/mm to about 5.00 1/mm, e.g., about 0.85 1/mm to about 4.90 1/mm, about 0.95 1/mm to about 4.80 1/mm, about 1.05 1/mm to about 4.70 1/mm, about 1.15 to about 4.60 1/mm, about 1.25 1/mm to about 4.50 1/mm, about 1.35 1/mm to about 4.40 1/mm, about 1.45 1/mm to about 4.30 1/mm, about 1.55 1/mm to about 4.20 l/mm, about 1.65 1/mm to about 4.10 1/mm, about 1.75 1/mm to about 4.00 1/mm, about 1.85 1/mm to about 3.9 1/mm, about 1.95 1/mm to about 3.80 1/mm, about 2.05 1/mm to about 3.70 1/mm, about 2.15 1/mm to about 3.60 1/mm, about 2.25 1 /mm to about 3.50 1/mm, about 2.35 1/mm to about 3.40 1/mm, about 2.45 1/mm to about 3.30 1/mm, about 2.55 1/mm to about 3.20 1/mm, about 2.65 1/mm to about 3.10 1/mm, about 2.75 1/mm to about 3.00 1/mm, or about 2.85 1/mm to about 2.90 1/mm.

In specific embodiments, an analyte sensor 100 as described herein has a sample chamber volume $V_c$ of less than about 0.50 mm³, e.g., less than about 0.40 mm³, less than about 0.30 mm³, less than about 0.20 mm³, less than about 0.1 mm³, less than about 0.075 mm³, or less than about 0.050 mm³. In some embodiments, an analyte sensor 100 as described herein has a sample chamber volume $V_c$ between about 0.50 mm³ and about 0.050 mm³.

Analyte sensors 100 having a relatively large surface area to volume ratio as described above may have benefits over conventional analyte sensors lacking the described relationship. For example, analyte sensors having the described surface area to volume ratio can be filled with sample significantly faster then conventional analyte sensors, thereby creating a true "touch-&-go" or "instant-fill" analyte sensor. For example, in some embodiments, an analyte sensor 100 provides for an elapsed time of 10 sec or less between initial fluid sample contact and analyte concentration determination, e.g. less than 9 sec, less than 8 sec, less than 7 sec, less than 6 sec, less than 5 sec, less than 4 sec, less than 3 sec, less than 2 sec, or less than 1 sec. In some embodiments, the elapsed time between initial fluid sample contact and analyte concentration determination is between 5 sec and 1 sec, e.g., about 4 sec, about 3 sec, or about 2 sec.

In addition, analyte sensors 100, such as those disclosed herein, having a relatively large sample port area may retain residual sample at the sample port when the analyte sensor is removed from the sample due to the surface tension of the sample. Given the relatively small sample chamber volume of the disclosed analyte sensors 100, the retained sample may have more than sufficient volume to complete filling of the sample chamber after the analyte sensor 100 is removed from the sample source. This may be beneficial as it can decrease the necessary contact time with the sample source and ensure complete sample chamber filling with relatively small sample volumes.

As described in greater detail in the Example below, conventional analyte sensors have $A_p/V_c$ ratios that are significantly less than those described for embodiments of the analyte sensors 100 disclosed herein, e.g., significantly less than about 0.75 1/mm.

Analyte Sensor Configurations

In some embodiments, as shown in FIG. 1A-FIG. 8, analyte sensor 100 has a generally rectangular shape, i.e., the sensor's length is greater than its width, although other shapes are possible. In one embodiment, the analyte sensor is in the form of a strip, i.e., the analyte sensor is an analytical test strip. The dimensions of the analyte sensor 100 may vary. In certain embodiments, the overall length of analyte sensor 100 may be no less than about 20 mm and no greater than about 50 mm. For example, the length may be between about 30 and 45 mm; e.g., about 30 to 40 mm. It should be understood, however that shorter and longer sensors could be made. In certain embodiments, the overall width of analyte sensor 100 may be no less than about 3 mm and no greater than about 15 mm. For example, the width may be between about 4 and 10 mm, about 5 to 8 mm, or about 5 to 6 mm. In one particular example, analyte sensor 100 has a length of about 32 mm and a width of about 6 mm. In another particular example, analyte sensor 100 has a length of about 40 mm and a width of about 5 mm. In yet another particular example, analyte sensor 100 has a length of about 34 mm and a width of about 5 mm.

As indicated above, the disclosed analyte sensors 100 include first and second substrates (101 and 102 respectively) which form the overall shape and size of analyte sensor 100. Substrates 101 and 102 may be substantially rigid or substantially flexible. In certain embodiments, substrates 101 and 102 are flexible or deformable. Examples of suitable materials for substrates 101 and 102 include, but are not limited to, polyester, polyethylene, polycarbonate, polypropylene, nylon, and other "plastics" or polymers. In certain embodiments the substrate material is "Melinex" polyester. Other non-conducting materials may also be used.

Substrate 101 includes first or proximal end 101A and second or distal end 101B. Similarly, substrate 102 includes first or proximal end 102A and second or distal end 102B. In the disclosed embodiments, one or more spacers 103 are positioned between substrate 101 and substrate 102.

The spacers 103, along with substrates 101 and 102, define the sample chamber 104. The spacers 103 are typically at least as flexible and deformable (or as rigid) as substrates 101 and 102. The spacer is typically constructed from an inert non-conducting material such as pressure-sensitive adhesive, polyester, Mylar™ Kevlar™ or any other strong, thin polymer film, or, alternatively, a thin polymer film such as a Teflon™ film, chosen for its chemical inertness.

In some embodiments, the spacers 103 include a layer or layers of adhesive, e.g., a spacer 103 can take the form of a double-sided adhesive tape (e.g., a carrier film with adhesive on opposing sides of the film). Any adhesive selected for spacer 103 should be selected to not diffuse or release material which may interfere with accurate analyte measurement. In some embodiments, the thickness of spacer 103 may be constant throughout, and may be at least about 0.01 mm (10 µm) and no greater than about 1 mm or about 0.5 mm. For example, the thickness may be between about 0.02 mm (20 µm) and about 0.2 mm (200 µm). In one embodiment, the thickness is about 0.05 mm (50 µm). In another embodiment the thickness is about 0.1 mm (100 µm).

Figure 3A:
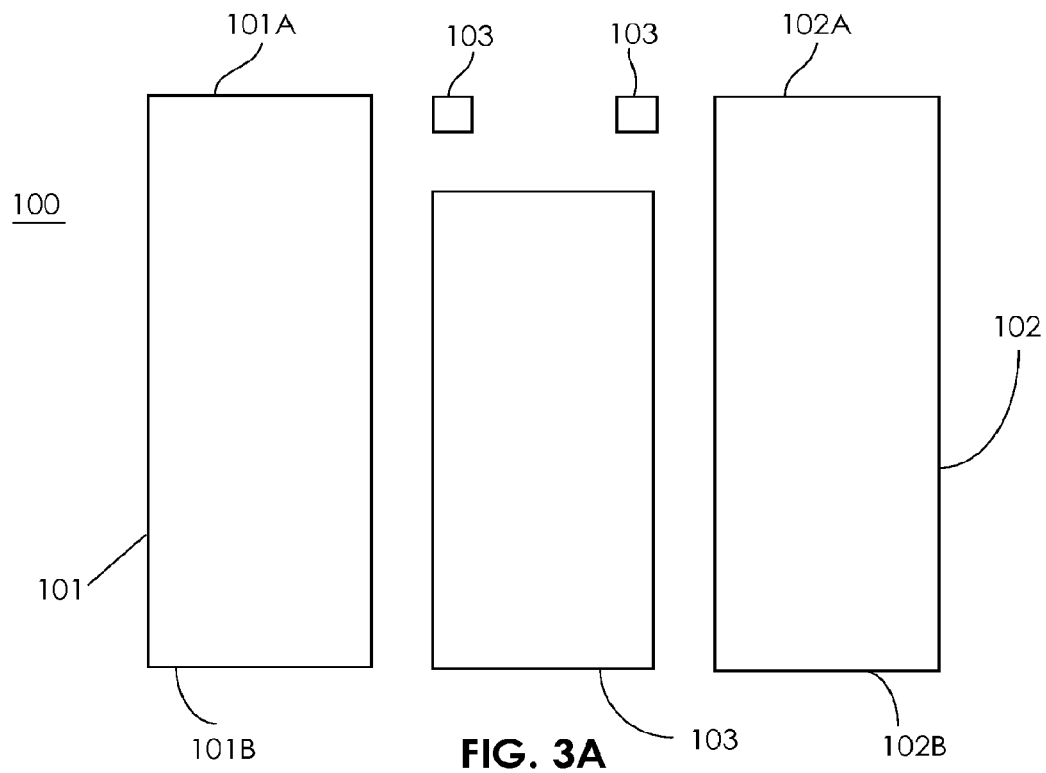
FIGS. 3A and 3B show another exemplary embodiment of an analyte sensor according to the present disclosure.
Figure 3B:
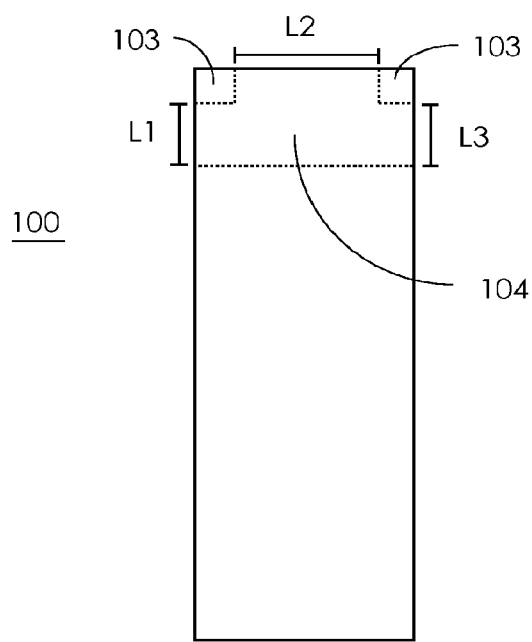
Figure 4:
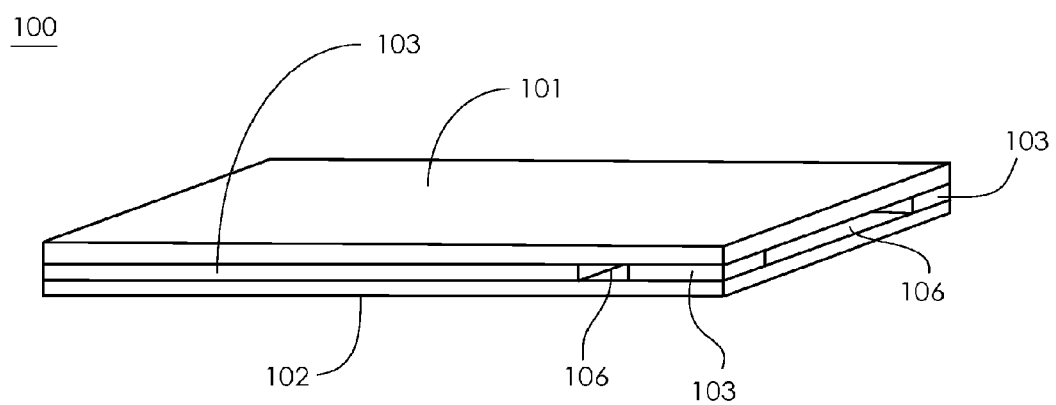
FIG. 4 shows a perspective view of the analyte sensor embodiment shown in FIGS. 3A and 3B.
Figures 5A, 5B:
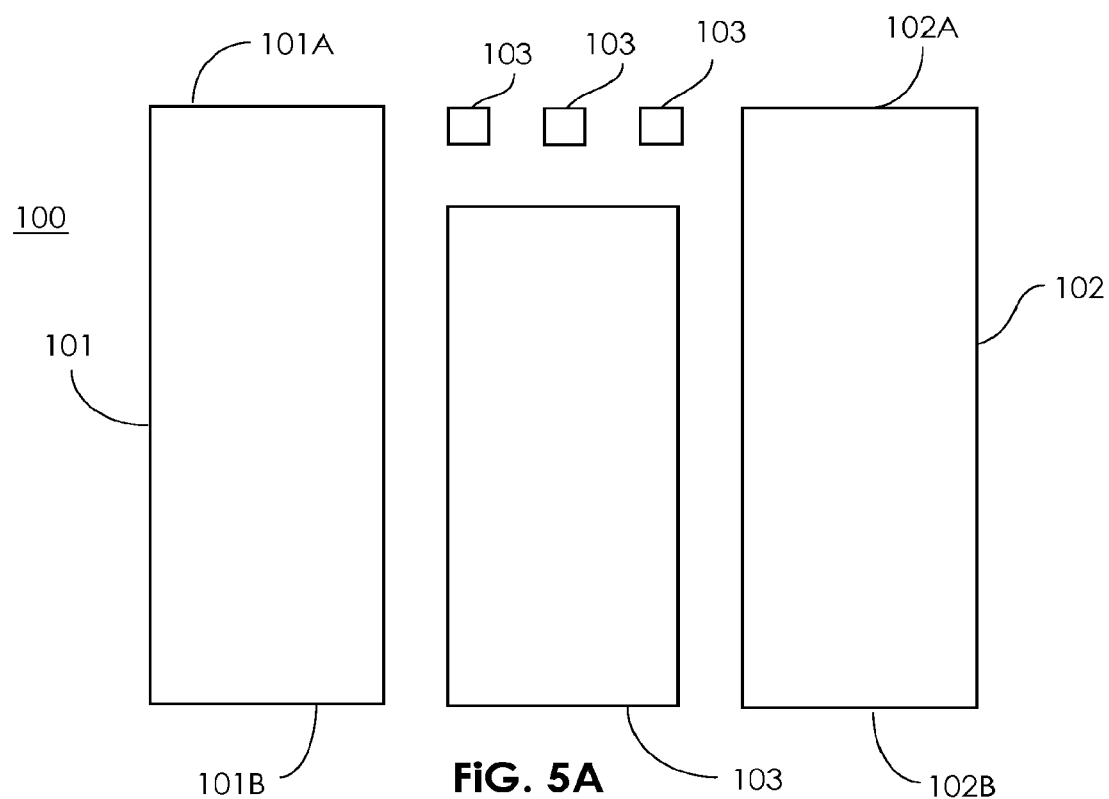
FIGS. 5A and 5B show another exemplary embodiment of an analyte sensor according to the present disclosure.
Figure 6:
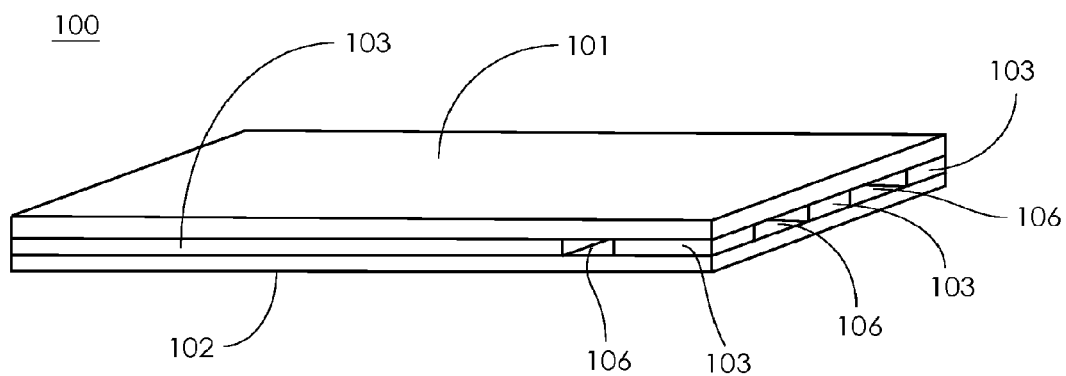
FIG. 6 shows a perspective view of the analyte sensor embodiment shown in FIGS. 5A and 5B.

In some embodiments, e.g., as depicted in FIGS. 3A, 3B, 4, 5A, 5B, 6, 7A, 7B, and 8, an analyte sensor 100 according to the present disclosure includes a plurality of spacers 103 positioned between the first substrate 101 and the second substrate 102. For example, FIGS. 3A, 3B and 4 depict an analyte sensor 100 which includes a total of three spacers 103 positioned between the first substrate 101 and the second substrate 102. FIGS. 5A, 5B and 6 depict an analyte sensor 100 which includes a total of four spacers 103 positioned between the first substrate 101 and the second substrate 102. As shown in the above referenced figures, a subset of the spacers 103 can be positioned at the sample loading end of analyte sensor 100. For example, in the embodiment shown in FIGS. 3A, 3B and 4, two of the three spacers 103 are positioned at the sample loading end of analyte sensor 100. In other words, two of the three spacers 103 are positioned between the proximal end 101A of the first substrate 101 and the proximal end 102A of the second substrate 102 in the assembled analyte sensor 100. Similarly, in the embodiment shown in FIGS. 5A, 5B and 6, three of the four spacers 103 are positioned at the sample loading end of analyte sensor 100. In other words, three of the four spacers 103 are positioned between the proximal end 101A of the first substrate 101 and the proximal end 102A of the second substrate 102 in the assembled analyte sensor 100. Such a configuration can provide greater strength and/or support to the structure of the analyte sensor relative to an analyte sensor lacking a spacer or spacers at the proximal end. For example, an analyte sensor lacking a spacer positioned at the proximal end may be susceptible to crushing and/or deformation of the sample chamber as a result of the handling of the analyte sensor.

In addition, analyte sensors having the above configurations can provide for multi-directional fill of the sample chamber 104 by providing a plurality of distinct sample fill areas which together make up the sample fill port 106. As used herein, the term "sample fill area" is used to describe a distinct portion of the sample fill port described previously herein. For example, with reference to FIGS. 3A, 3B and 4, the sample fill port can be described as being made up of three sample fill areas each having an area (A). For illustration, in the embodiment shown in FIGS. 3A, 3B and 4, the three sample fill areas have areas (A) equal to L1×(h), L2×(h), and L3×(h) respectively, where (h) is the height of the sample chamber.

In one embodiment, an analyte sensor 100 includes a first substrate 101 having a proximal end 101A and a distal end 101B. The analyte sensor 100 also includes a second substrate 102 having a proximal end 102A and a distal end 102B. A plurality of spacers 103 are positioned between the first substrate 101 and the second substrate 102 in a single plane. The first substrate 101, the second substrate 102, and the plurality of spacers 103 together define a sample chamber 104, and the plurality of spacers 103 are positioned such that a plurality of sample fill areas are provided through which the sample chamber can be simultaneously filled with a sample. Thus, in the above embodiment, the configuration of the spacers 103 in the analtye sensor 100 allows for simultaneous or near simultaneous filling of the sample chamber 400 from multiple sample fill areas.

Supported Tip Protrusions

Figure 7A:
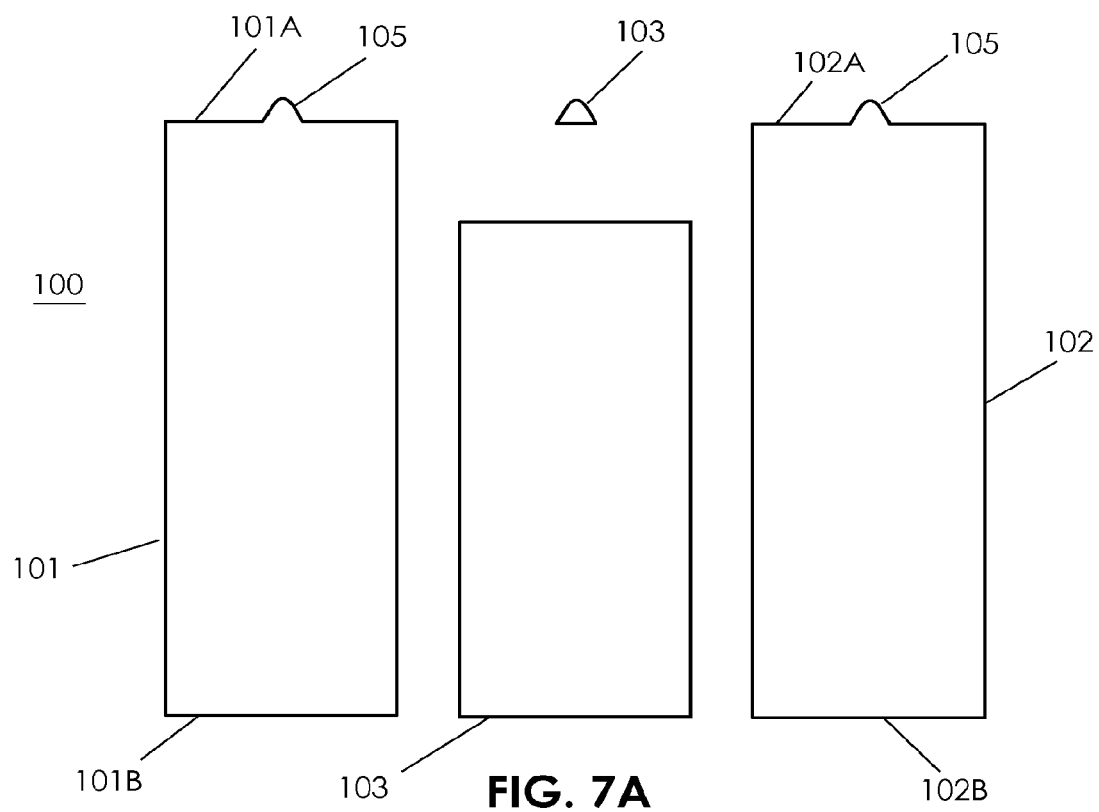
FIGS. 7A and 7B show another exemplary embodiment of an analyte sensor according to the present disclosure.
Figure 7B:
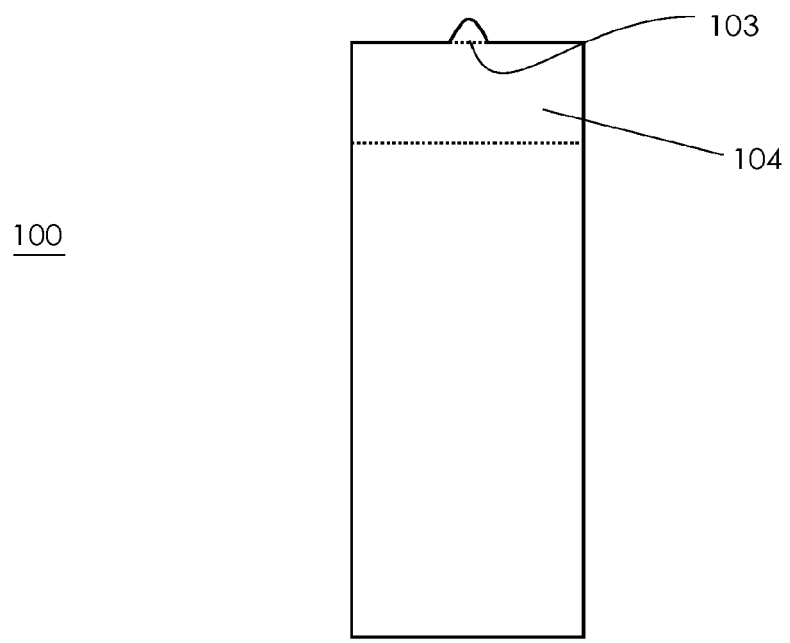
Figure 8:
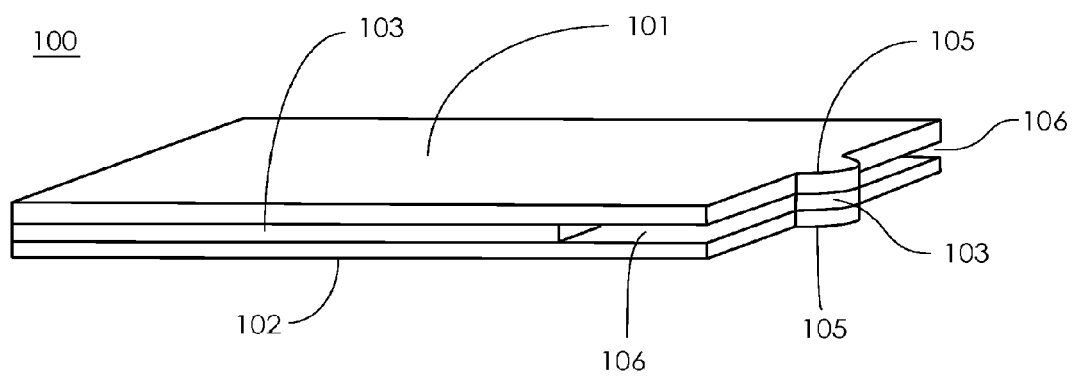
FIG. 8 shows a perspective view of the analyte sensor embodiment shown in FIGS. 7A and 7B.

In some embodiments, e.g., as shown in FIGS. 7A, 7B and 8, a spacer 103 can be positioned between a particular structure of substrate 101 and 102. For example, a spacer 103 can be positioned between a protrusion 105 present on substrate 101 and a protrusion 105 present on substrate 102. Protrusions are commonly used in the art as fill-assist structures which can facilitate uptake of a fluid sample. Additional fill assist structures are described below and in U.S. Patent Application Publication No. 2008/0267823, the disclosure of which is incorporated by reference herein; and in U.S. patent application Ser. No. 11/461,725, filed Aug. 1, 2006, the disclosure of which is incorporated by reference herein.

In some embodiments, e.g., as shown in FIGS. 7A, 7B and 8, a first spacer 103 is positioned between a protrusion 105 present on substrate 101 and a protrusion 105 present on substrate 102, but is not positioned between any other portions of substrate 101 and substrate 102. In other words, the first spacer 103, which is positioned between the two protrusions 105, is located only between the protrusions 105 and does not extend beyond the area positioned between protrusions 105. It should be noted that this does not exclude the use of a second spacer 103, which is not positioned between protrusions 105, but is positioned between substrate 101 and substrate 102, e.g., as shown in FIGS. 7A, 7B and 8. In some embodiments, the first spacer 103 positioned between protrusions 105 can be described as defining an area that is coextensive with the area defined by the protrusions 105.

The presence of a spacer 103 between protrusions 105 or other fill assist structures provides structural support for the protrusions 105 or other fill assist structures. This can be important, for example, to prevent crushing and/or deformation of the sample chamber which can occur during normal use and handling of conventional analyte sensors lacking supported protrusions or other fill assist structures.

Working Electrode

As summarized previously herein, an analyte sensor 100 includes a working electrode (not shown), and a reference/counter electrode (not shown) positioned at least partially in the sample chamber 104. The working electrode may be formed from a molded carbon fiber composite or it may consist of an inert non-conducting base material, such as polyester, upon which a suitable conducting layer is deposited. The conducting layer should have relatively low electrical resistance and should be electrochemically inert over the potential range of the sensor during operation. Suitable conductors include gold, carbon, platinum, ruthenium dioxide and palladium, as well as other non-corroding materials known to those skilled in the art. The working electrode can be a combination of two or more conductive materials. An example of a suitable conductive epoxy is ECCOCOAT CT5079-3 Carbon-Filled Conductive Epoxy Coating (available from W.R. Grace Company, Woburn, Mass.).

The working electrode can be applied on substrate 101 and/or 102 by any of a variety of methods, including by being deposited, such as by vapor deposition or vacuum deposition or otherwise sputtered, printed on a flat surface or in an embossed or otherwise recessed surface, transferred from a separate carrier or liner, etched, or molded. Suitable methods of printing include screen-printing, piezoelectric printing, ink jet printing, laser printing, photolithography, painting, gravure roll printing, transfer printing, and other known printing methods.

Optionally, a non-conductive material, such as a non-conductive ink, can be deposited adjacent the working electrode to provide a planar surface along the path of travel of the sample fluid. The non-conductive material is suitable for creating a smooth surface to facilitate filling by capillary action and/or for reducing the likelihood that air bubbles will become entrapped near the working electrode. This non-conductive material can be colored or colorless and may be formed on the substrate by printing or other techniques. The non-conductive material may be deposited prior to or subsequent to the formation of the working electrode.

Reference/Counter Electrode

The reference/counter electrode may be constructed in a manner similar to the working electrode. As used herein, the term "reference/counter electrode" refers to an electrode that functions as a reference electrode, a counter electrode, or both a reference electrode and a counter electrode. The reference/counter electrode can be formed, for example, by depositing carbon or other electrode material onto substrate 101 and/or 102. The material of the reference/counter electrode may be deposited by a variety of methods such as those described above for the working electrode. Suitable materials for the reference/counter electrode include Ag/AgCl or Ag/AgBr printed on a non-conducting substrate.

Optionally, a non-conductive material may be deposited adjacent to the reference/counter electrode and/or between the working electrode and the reference/counter electrode to provide a planar surface along the path of travel of the sample fluid. The non-conductive material is suitable for creating a smooth surface to facilitate filling by capillary action and/or for reducing the likelihood that air bubbles will become entrapped between or near the reference/counter electrode.

This non-conductive material can be colored or colorless and may be formed on the by printing or other techniques. The non-conductive material may be deposited prior to or subsequent to the formation of the reference/counter electrode.

Electrode Configuration

A variety of analyte sensor electrode configurations are known in the art which may be suitable for use in the disclosed analyte sensors 100. For example, suitable configurations can include configurations having a working electrode positioned in opposition to a reference/counter electrode or configurations having the working electrode positioned coplanar with the reference/counter electrode. Additional suitable electrode configurations include, but are not limited to, those described in U.S. patent application Ser. No. 11/461,725, filed Aug. 1, 2006; U.S. patent application Ser. No. 12/102,374, filed Apr. 14, 2008; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. Patent Application Publication No. 2009/0095625; U.S. Pat. No. 6,616,819; U.S. Pat. No. 6,143,164; and U.S. Pat. No. 6,592,745; the disclosures of each of which are incorporated by reference herein.

Analytes

A variety of analytes can be detected and quantified using the analyte sensors disclosed herein including, but not limited to, glucose, blood (3-ketone, ketone bodies, lactate, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin, in sample of body fluid. Analyte sensors may also be configured to detect and/or quantify drugs, such as, for example, antibiotics (e.g., gentamicin, vancomycin, and the like), digitoxin, digoxin, drugs of abuse, theophylline, and warfarin. Assays suitable for determining the concentration of DNA and/or RNA are disclosed in U.S. Pat. No. 6,281,006 and U.S. Pat. No. 6,638,716, the disclosures of each of which are incorporated by reference herein.

Analyte-Responsive Enzyme

The disclosed analyte sensors include a measurement zone (not shown) which includes an analyte-responsive enzyme which is capable of transferring electrons to or from a redox mediator and the analyte. For example, a glucose oxidase (GOD) or glucose dehydrogenase (GDH) can be used when the analyte is glucose. A lactate oxidase can be used when the analyte is lactate. These enzymes catalyze the electrolysis of an analyte by transferring electrons between the analyte and the electrode via the redox mediator. In one embodiment, the analyte-responsive enzyme is immobilized on the working electrode. This is accomplished, for example, by cross linking the analyte-responsive enzyme with a redox mediator on the working electrode, thereby providing a sensing layer on the working electrode. In an alternative embodiment, the analyte-responsive enzyme is disposed adjacent to the electrode. Generally, the analyte-responsive enzyme and redox mediator are positioned in close proximity to the working electrode in order to provide for electrochemical communication between the analyte-responsive enzyme and redox mediator and the working electrode. Generally, the analyte-responsive enzyme and redox mediator are positioned relative to the reference/counter electrode such that electrochemical communication between the analyte-responsive enzyme and the redox mediator and the reference/counter electrode is minimized Additional analyte-responsive enzymes and cofactors which may be used in connection with the disclosed analyte sensors are described in U.S. Pat. No. 6,736,957, the disclosure of which is incorporated by reference herein.

In some embodiments, in order to facilitate the electrochemical reaction of the analyte sensor the measurement zone also includes an enzyme co-factor. For example, where the analyte-responsive enzyme is GDH suitable cofactors include pyrroloquinoline quinone (PQQ), nicotinamide adenine dinucleotide NAD and flavin adenine dinucleotide (FAD).

Redox Mediator

In addition to the analyte-responsive enzyme, the measurement zone includes a redox mediator. In one embodiment, the redox mediator is immobilized on the working electrode. Materials and methods for immobilizing a redox mediator on an electrode are provided in U.S. Pat. No. 6,592,745, the disclosure of which is incorporated by reference herein. In an alternative embodiment, the redox mediator is disposed adjacent to the working electrode.

The redox mediator mediates a current between the working electrode and the analyte when present. The mediator functions as an electron transfer agent between the electrode and the analyte.

Almost any organic or organometallic redox species can be used as a redox mediator. In general, suitable redox mediators are rapidly reducible and oxidizable molecules having redox potentials a few hundred millivolts above or below that of the standard calomel electrode (SCE), and typically not more reducing than about −100 mV and not more oxidizing than about +400 mV versus SCE. Examples of organic redox species are quinones and quinhydrones and species that in their oxidized state have quinoid structures, such as Nile blue and indophenol. Unfortunately, some quinones and partially oxidized quinhydrones react with functional groups of proteins such as the thiol groups of cysteine, the amine groups of lysine and arginine, and the phenolic groups of tyrosine which may render those redox species unsuitable for some of the sensors of the present invention, e.g., sensors that will be used to measure analyte in biological fluids such as blood.

In general, mediators suitable for use in the invention have structures which prevent or substantially reduce the diffusional loss of redox species during the period of time that the sample is being analyzed. The preferred redox mediators include a redox species bound to a polymer which can in turn be immobilized on the working electrode. Useful redox mediators and methods for producing them are described in U.S. Pat. Nos. 5,262,035; 5,264,104; 5,320,725; 5,356,786; 6,592,745; and 7,501,053, the disclosure of each of which is incorporated by reference herein. Although, any organic or organometallic redox species can be bound to a polymer and used as a redox mediator, the preferred redox species is a transition metal compound or complex. The preferred transition metal compounds or complexes include osmium, ruthenium, iron, and cobalt compounds or complexes. The most preferred are osmium compounds and complexes.

One type of non-releasable polymeric redox mediator contains a redox species covalently bound in a polymeric composition. An example of this type of mediator is poly(vinylferrocene).

Alternatively, a suitable non-releasable redox mediator contains an ionically-bound redox species. Typically, these mediators include a charged polymer coupled to an oppositely charged redox species. Examples of this type of mediator include a negatively charged polymer such as Nafion® (Dupont) coupled to a positively charged redox species such as an osmium or ruthenium polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide.

In another embodiment of the invention, the suitable non-releasable redox mediators include a redox species coordinatively bound to the polymer. For example, the mediator may be formed by coordination of an osmium or cobalt 2,2'-bipyridyl complex to poly(1-vinyl imidazole) or poly(4-vinyl pyridine).

The preferred redox mediators are osmium transition metal complexes with one or more ligands having a nitrogen-containing heterocycle such as 2,2'-bipyridine, 1,10-phenanthroline or derivatives thereof. Furthermore, the preferred redox mediators also have one or more polymeric ligands having at least one nitrogen-containing heterocycle, such as pyridine, imidazole, or derivatives thereof. These preferred mediators exchange electrons rapidly between each other and the electrodes so that the complex can be rapidly oxidized and reduced.

In particular, it has been determined that osmium cations complexed with two ligands containing 2,2'-bipyridine, 1,10-phenanthroline, or derivatives thereof, the two ligands not necessarily being the same, and further complexed with a polymer having pyridine or imidazole functional groups form particularly useful redox mediators in the small volume sensors of the present invention. Preferred derivatives of 2,2'-bipyridine for complexation with the osmium cation are 4,4'-dimethyl-2,2'-bipyridine and mono-, di-, and polyalkoxy-2,2'-bipyridines, such as 4,4'-dimethoxy-2,2'-bipyridine, where the carbon to oxygen ratio of the alkoxy groups is sufficient to retain solubility of the transition metal complex in water. Preferred derivatives of 1,10-phenanthroline for complexation with the osmium cation are 4,7-dimethyl-1,10-phenanthroline and mono-, di-, and polyalkoxy-1,10-phenanthrolines, such as 4,7-dimethoxy-1,10-phenanthroline, where the carbon to oxygen ratio of the alkoxy groups is sufficient to retain solubility of the transition metal complex in water. Exemplary polymers for complexation with the osmium cation include poly(1-vinyl imidazole), e.g., PVI, and poly(4-vinyl pyridine), e.g., PVP, either alone or with a copolymer. Most preferred are redox mediators with osmium complexed with poly(1-vinyl imidazole) alone or with a copolymer.

Suitable redox mediators have a redox potential between about −150 mV to about +400 mV versus the standard calomel electrode (SCE). For example, the potential of the redox mediator can be between about −100 mV and +100 mV, e.g., between about −50 mV and +50 mV. In one embodiment, suitable redox mediators have osmium redox centers and a redox potential more negative than +100 mV versus SCE, e.g., the redox potential is more negative than +50 mV versus SCE, e.g., is near −50 mV versus SCE.

In one embodiment, the redox mediators of the disclosed analyte sensors are air-oxidizable. This means that the redox mediator is oxidized by air, e.g., so that at least 90% of the mediator is in an oxidized state prior to introduction of sample into the sensor. Air-oxidizable redox mediators include osmium cations complexed with two mono-, di-, or polyalkoxy-2,2'-bipyridine or mono-, di-, or polyalkoxy-1,10-phenanthroline ligands, the two ligands not necessarily being the same, and further complexed with polymers having pyridine and imidazole functional groups. In particular, $Os[4,4'\text{-dimethoxy-2,2'-bipyridine}]_2Cl^{+/+2}$ complexed with poly(4-vinyl pyridine) or poly(1-vinyl imidazole) attains approximately 90% or more oxidation in air.

In one specific embodiment, the redox mediator is 1,10 Phenanthrolene-5,6-dione (PQ).

To prevent electrochemical reactions from occurring on portions of the working electrode not coated by the mediator, a dielectric may be deposited on the electrode over, under, or surrounding the region with the bound redox mediator. Suitable dielectric materials include waxes and non-conducting organic polymers such as polyethylene. Dielectric may also cover a portion of the redox mediator on the electrode. The covered portion of the mediator will not contact the sample, and, therefore, will not be a part of the electrode's working surface.

Although it can be advantageous to minimize the amount of redox mediator used, the range for the acceptable amount of redox mediator typically has a lower limit. The minimum amount of redox mediator that may be used is the concentration of redox mediator that is necessary to accomplish the assay within a desirable measurement time period, for example, no more than about 5 minutes or no more than about 1 minute.

The analyte sensor can be configured (e.g., by selection of redox mediator, positioning of electrodes, etc.) such that the sensor signal is generated at the working electrode with a measurement period of no greater than about 5 minutes and such that a background signal that is generated by the redox mediator is no more than five times a signal generated by oxidation or reduction of 5 mM glucose. In some embodiments, the analyte sensor is configured such that the background signal that is generated by the redox mediator is the same or less than the signal generated by oxidation or reduction of 5 mM glucose. In some embodiments, the background that is generated by the redox mediator is no more than 25% of the signal generated by oxidation or reduction of 5 mM glucose, e.g., no more than 20%, no more than 15% or no more than 5%.

Measurement Zone

As discussed above, measurement zone (not shown) of analyte sensor 100 is configured such that when a sample is provided in the measurement zone the sample is in electrolytic contact with the working electrode (not shown) and the reference/counter electrode (not shown). The measurement zone is typically defined by a combination of a working electrode, a reference/counter electrode, substrate 101, substrate 102, and one or more spacers 103. The measurement zone is a region of the sample chamber 104 that contains that portion of the sample that is exposed to the analyte-responsive enzyme and redox mediator during the analyte assay. For example, where a portion of the sample contacts one or more of the electrodes but is not exposed to the analyte-responsive enzyme and redox mediator (e.g., because of the presence of a dielectric coating on the electrode), the unexposed portion is not included in the measurement zone. In some embodiments, the sample chamber and the measurement zone are coextensive. Additional description with respect to sample chambers and measurement zones is provided, for example, in U.S. Pat. Nos. 6,299,757; 6,338,790; 6,461,496; 6,591,125; 6,592,745; 6,618,934; 7,225,535; 7,550,069 and 7,563,350; and U.S. Patent Application Publication Nos.: US2006/0169599; US2007/0193019; and US2009/0014328; the disclosures of each of which are incorporated by reference herein.

Sorbent Material

The sample chamber 104 may be empty prior to entry of the sample. Optionally, the sample chamber 104 can include a sorbent material to sorb and hold a fluid sample during detection and/or analysis. Suitable sorbent materials include polyester, nylon, cellulose, and cellulose derivatives such as nitrocellulose. The sorbent material facilitates the uptake of small volume samples by a wicking action which may complement or replace any capillary action of the sample chamber 104. In addition or alternatively, a portion or the entirety of the wall of the sample chamber may be covered by a surfactant, such as, for example, Zonyl FSO.

In some embodiments, the sorbent material is deposited using a liquid or slurry in which the sorbent material is dissolved or dispersed. The solvent or dispersant in the liquid or slurry may then be driven off by heating or evaporation processes. Suitable sorbent materials include, for example, cellulose or nylon powders dissolved or dispersed in a suitable solvent or dispersant, such as water. The particular solvent or dispersant should also be compatible with the material of the electrodes (e.g., the solvent or dispersant should not dissolve the electrodes).

One of the functions of the sorbent material is to reduce the volume of fluid needed to fill the sample chamber 104 of the analyte sensor 100. The actual volume of sample within the sample chamber is partially determined by the amount of void space within the sorbent material. Typically, suitable sorbents consist of about 5% to about 50% void space. In one embodiment, the sorbent material consists of about 10% to about 25% void space.

The displacement of fluid by the sorbent material is advantageous. By addition of a sorbent, less sample is needed to fill the sample chamber. This reduces the volume of sample that is required to obtain a measurement and also reduces the time required to electrolyze the sample.

The sorbent material may include a tab which is made of the same material as the sorbent and which extends from the analyte sensor 100, or from an opening in the analyte sensor 100, so that a sample may be brought into contact with the tab, sorbed by the tab, and conveyed into the sample chamber 104 by the wicking action of the sorbent material. This provides a method for directing the sample into the sample chamber. For example, the analyte sensor 100 may be brought into contact with a region of an animal (including human) that has been pierced with a lancet to draw blood. The blood is brought in contact with the tab and drawn into sample chamber 104 by the wicking action of the sorbent. The direct transfer of the sample to the sensor is especially important when the sample is very small, such as when the lancet is used to pierce a portion of the animal that is not heavily supplied with near-surface capillary vessels and furnishes a blood sample volume of 1 µL or less.

Methods other than the wicking action of a sorbent may be used to transport the sample into the sample chamber 104. Examples of such methods for transport include the application of pressure on a sample to push it into the sample chamber 104, the creation of a vacuum by a pump or other vacuum-producing method to pull the sample into the sample chamber 104, capillary action due to interfacial tension of the sample with the walls of a thin sample chamber 104.

Other filler materials may be used to fill the sample chamber 104 and reduce the sample volume. For example, glass beads can be deposited in the sample chamber 104 to occupy space. In exemplary embodiments, these filler materials are hydrophilic so that the body fluid can easily flow into the sample chamber 104. In some cases, such as glass beads with a high surface area, these filler materials may also wick the body fluid into the sample chamber 104 due to their high surface area and hydrophilicity.

Fill Assist

The analyte sensors 100 can be configured for top-filling, tip-filling, corner-filling and/or side-filling. In some embodiments, the analyte sensors 100 include one or more optional fill assist structures, e.g., one or more notches, cut-outs, indentations, and/or protrusions, which facilitate the collection of the fluid sample. For example, the analyte sensor 100 can be configured such that the proximal end of the analyte sensor is narrower than the distal end of the analyte sensor. In one such embodiment, the analyte sensor includes a tapered tip at the proximal end of the analyte sensor, e.g., the end of the analyte sensor 100 that is opposite from the end that engages with a meter.

The analyte sensors 100 can be configured to include one or more protrusions 105 which facilitate filling of the analyte sensors 100. One such embodiment is shown in FIGS. 7A, 7B and 8, wherein substrates 101 and 102 include proximal end protrusions 105. As discussed previously herein, in some embodiments the analyte sensors 100 include one or more spacers 103 positioned with respect to protrusions 105 such that they provide structural support for the protrusions 105. Additional fill assist structures are described in U.S. Patent Publication No. 2008/0267823, the disclosure of which is incorporated by reference herein; and U.S. patent application Ser. No. 11/461,725, filed Aug. 1, 2006, the disclosure of which is incorporated by reference herein.

Insertion Monitors and Turn-on/Selection Monitors

In some embodiments, analyte sensors 100 include an optional insertion monitor as described for example in U.S. Pat. No. 6,616,819, the disclosure of which is incorporated by reference herein; and/or a turn-on/selection monitor as described, for example, in U.S. application Ser. No. 12/431,672, filed Apr. 28, 2009, and entitled "Smart Sensor Ports and Methods of Using Same," the disclosure of which is incorporated by reference herein. Additional description of insertion monitors and configurations suitable for use as turn-on/selection monitors is provided, for example, in U.S. Patent Application Publication No. US2006/0091006; U.S. Patent Application Publication No. US2008/0267823; U.S. Patent Application Publication No. US2009/0011449; U.S. Patent Application Publication No. US2008/0066305; U.S. Patent Application Publication No. US2008/0060196; U.S. Pat. Nos. 6,592,745; 6,143,164; 6,071,391; 6,503,381; and U.S. Pat. No. 6,893,545; the disclosures of each of which are incorporated by reference herein.

Fill-Indicator Electrodes

In some embodiments, an analyte sensor 100 includes one more optional fill-indicator electrodes. Such indicator electrodes are well known in the art and can be used to indicate when a measurement zone of an analyte sensor 100 is filled with sample. Description of fill-indicator electrodes is provided, for example, in U.S. Pat. Nos. 6,592,745; and 6,616,819; the disclosures of each of which are incorporated by reference herein.

Methods of Making Supported Analyte Sensors

With reference to FIGS. 9A-9D, methods of making the analyte sensors 100 are now described. Each of FIGS. 9A-9D has a left and right side, wherein the left side shows a top view of a plurality of spacers 103 positioned between a first substrate 101 and a second substrate 102. The referenced figures provide a view through the depicted structures such that the location of spacers 103 can be seen. For reference, spacers 103 are shown bounded by dashed lines. The outline 107 of the analyte sensor 100 to be formed is shown for reference in the left hand side of each of the referenced figures. The right side shows a top view of the form of analyte sensor 100 following removal of excess portions of spacer 103 and first and second substrates 101 and 102.

In one embodiment, as exemplified by FIG. 9A, a method of making an analyte sensor 100, includes combining a first substrate 101 having a proximal end 101A and a distal end 101B, a second substrate 102 having a proximal end 102A and a distal end 102B, and a plurality of spacers 103. This combination provides a layered structure 108 having the plurality of spacers 103 positioned in a plane between the first substrate 101 and the second substrate 102.

Subsequently, material from the layered structure 108 is removed to provide an analyte sensor 100 having a first protrusion 105 at the proximal end 101A of the first substrate 101 and a second protrusion 105 (not visible in FIG. 9A) at the proximal end 102A of the second substrate 102, wherein the first protrusion 105 and the second protrusion 105 are supported by one of the plurality of spacers 103, or a portion thereof, positioned between the first protrusion 105 and the second protrusion 105.

In one embodiment, as exemplified by FIG. 9B, the removing step includes removing material from the layered structure 108 to provide a third protrusion 105 at the proximal end 101A of the first substrate 101 and a fourth protrusion 105 (not visible in FIG. 9B) at the proximal end 102A of the second substrate 102, wherein the third protrusion 105 and the fourth protrusion 105 are supported by one of the plurality of spacers 103, or a portion thereof, positioned between the third protrusion 105 and the fourth protrusion 105.

In one embodiment, as exemplified by FIGS. 9C and 9D, a method of making an analyte sensor 100 is described, wherein the method includes combining a first substrate 101 having a proximal end 101A and a distal end 101B, a second substrate 102 having a proximal end 102A and a distal end 102B, and a plurality of spacers 103. This combination provides a layered structure 108 having the plurality of spacers 103 positioned in a plane between the first substrate 101 and the second substrate 102.

Subsequently, material from the layered structure 108 is removed to provide an analyte sensor 100 having a first portion of one of the plurality of spacers 103 positioned between the proximal end 101A of the first substrate 101 and the proximal end 102A of the second substrate 102, and a second portion of the spacer 103 positioned between the proximal end 101A of the first substrate 101 and the proximal end 102A of the second substrate 102, wherein the first and second portions of the spacer 103 are not in contact, e.g., where they are separated by a region of sensor port 106.

As shown, in FIGS. 9C and 9D, a spacer 103 can be configured to have a shape which provides for separation of portions of the spacer 103 following removal of material from layered structure 108. In some embodiments, as exemplified in FIG. 9C, one of the plurality of spacers 103, e.g., a spacer 103 positioned between the proximal end 101A of the first substrate 101 and the proximal end 102A of the second substrate 102, includes a spacer which includes an edge defining a repeating geometric pattern. Where a spacer 103 having such a repeating geometric pattern is utilized, removal of material from the layered structure 108 can provide discrete, unconnected regions of spacer 103, which in turn provide support for the proximal end of analyte sensor 100 and partially define sample chamber 104. A spacer 103 having a repeating geometric pattern, e.g., a spacer 103 positioned between the proximal end 101A of the first substrate 101 and the proximal end 102A of the second substrate 102, can also be utilized to provide discrete, unconnected regions of spacer 103 which are positioned between one or more pairs of protrusions 105 thereby providing support for the one or more pairs of protrusions 105. A variety of suitable geometric shapes and patterns which can be used for spacer 103 are known in the art, including, for example, sawtooth patterns, wave patterns and crenellation patterns.

A variety of methods are known in the art which can be used to remove excess material from layered structure 108 in order to provide analyte sensor 100. Such methods include, but are not limited to, punching; cutting; e.g., laser cutting; etc.

In one embodiment, the plurality of spacers 103 are deposited as a single layer on first substrate 101 or second substrate 102, e.g., a single layer of adhesive double sided tape may be used.

During preparation of an analyte sensor 100 according to the above methods, substrate 101, substrate 102 and placers 103 can be positioned in the layered structure 108 such that upon removal of excess material from layered structure 108, an analyte sensor 100 having a sample chamber 104 and a sample fill port 106 is produced, wherein the sample chamber has a volume ($V_c$) in mm$^3$, the sample fill port has an area ($A_p$) in mm$^2$ and $A_p/V_c$ is greater than about 0.75 1/mm, e.g., greater than about 1.0 1/mm, greater than about 1.5 1/mm, greater than about 2.0 1/mm, greater than about 2.5 1/mm, or greater than about 3.0 1/mm Similarly, during preparation of an analyte sensor 100 according to the above methods, substrate 101, substrate 102 and placers 103 can be positioned in the layered structure 108 such that upon removal of excess material from layered structure 108, an analyte sensor 100 having a sample chamber 104 is provided, wherein the sample chamber 104 has a $V_e$ of less than 0.10 mm$^3$, e.g., less than 0.075 mm$^3$, or less than 0.050 mm$^3$.

Methods of Using Analyte Sensors

The sensors described herein find use in methods for determining the concentration of an analyte in a fluid sample from a subject. Generally, these methods include inserting an analyte sensor 100 into an analyte meter or other suitable device (not shown); contacting a fluid sample, e.g. a blood sample, with the analyte sensor; generating a sensor signal at the working electrode; and determining the concentration of the analyte using the generated sensor signal.

A variety of analyte meters and other suitable devices are known in the art which may be suitable for use with the disclosed analyte sensors 100, and, in some embodiments, an analyte sensor 100 may be specifically configured for use with one of these analyte meters or other devices. Suitable analyte meters and other devices may include, for example, those described in U.S. Pat. Nos. 7,041,468; 5,356,786; 6,175,752; 6,560,471; 5,262,035; 6,881,551; 6,121,009; 7,167,818; 6,270,455; 6,161,095; 5,918,603; 6,144,837; 5,601,435; 5,822,715; 5,899,855; 6,071,391; 6,120,676; 6,143,164; 6,299,757; 6,338,790; 6,377,894; 6,600,997; 6,773,671; 6,514,460; 6,592,745; 5,628,890; 5,820,551; 6,736,957; 4,545,382; 4,711,245; 5,509,410; 6,540,891; 6,730,200; 6,764,581; 6,299,757; 6,461,496; 6,503,381; 6,591,125; 6,616,819; 6,618,934; 6,676,816; 6,749,740; 6,893,545; 6,942,518; 6,514,718; 5,264,014; 5,262,305; 5,320,715; 5,593,852; 6,746,582; 6,284,478; 7,299,082; U.S. Patent Application No. 61/149,639, entitled "Compact On-Body Physiological Monitoring Device and Methods Thereof", U.S. patent application Ser. No. 11/461,725, filed Aug. 1, 2006, entitled "Analyte Sensors and Methods"; U.S. patent application Ser. No. 12/495,709, filed Jun. 30, 2009, entitled "Extruded Electrode Structures and Methods of Using Same"; U.S. Patent Application Publication No. US2004/0186365; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No.

2008/0102441; U.S. Patent Application Publication No. 2008/0066305; U.S. Patent Application Publication No. 2007/0199818; U.S. Patent Application Publication No. 2008/0148873; and U.S. Patent Application Publication No. 2007/0068807; the disclosures of each which are incorporated by reference herein.

Examples of specific electrochemical reactions which can be utilized to produce a sensor signal are described in detail in U.S. Pat. No. 6,592,745, the disclosure of which is incorporated by reference herein.

In one embodiment, the determining step includes determining the concentration of the analyte by amperometry, coulometry, potentiometry, and/or voltametry, including square wave voltametry, using the analyte sensor 100.

In one embodiment, the method includes a medication dosage determination step. For example, where the analyte is glucose, the method can include a determination step in which an algorithm is performed to determine an insulin dose, e.g., a bolus insulin dose, based on the concentration of glucose in the sample.

In another embodiment, the method includes an administering step wherein a medication dose, e.g., an insulin dose, determined according to the method is administered to the subject via a medication delivery device, e.g., a needle, syringe, pump, catheter, inhaler, transdermal patch, or combination thereof.

In another embodiment, the administering step includes administering a medication dose, e.g., an insulin dose, determined according to the method to the subject via a medication delivery device positioned at a distance from the analyte meter and in communication with the analyte meter.

EXAMPLE

The following example is set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

$A_p/V_c$ Values for Disclosed Analyte Sensors Vs. Conventional Analyte Sensors

In order to demonstrate that analyte sensors disclosed herein have $A_p/V_c$ values significantly greater than conventional analyte sensors, appropriate measurements were made and $A_p/V_c$ values were calculated for 14 conventional analyte test strips (designated A-N). These values were compared with $A_p/V_c$ values calculated for two exemplary analyte sensors according to the present disclosure (designated as O and P in the Table below).

TABLE

| Strip ID | $L_p$ (mm) | $A_c$ (mm2) | $L_p/A_c$ (1/mm) |
|---|---|---|---|
| A | 2.11 | 8.25 | 0.26 |
| B | 1.50 | 5.33 | 0.28 |
| C | 2.65 | 4.81 | 0.55 |
| D | 1.22 | 4.10 | 0.30 |
| E | 1.29 | 3.56 | 0.36 |
| F | 1.74 | 4.55 | 0.38 |
| G | 2.04 | 6.19 | 0.32 |
| H | 1.52 | 6.50 | 0.23 |
| I | 2.74 | 11.17 | 0.25 |
| J | 1.34 | 4.51 | 0.30 |
| K | 1.37 | 4.51 | 0.30 |
| L | 1.36 | 3.58 | 0.38 |
| M | 0.98 | 1.67 | 0.58 |
| N | 1.19 | 2.84 | 0.42 |
| O | 3.29 | 1.94 | 1.70 |
| P | 3.82 | 1.16 | 3.29 |

As indicated in the Table above, $A_p/V_c$ values (expressed as $L_p/A_p$) for the two exemplary disclosed analyte sensors O and P were significantly greater than those for the conventional analyte test strips A-N.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. An analyte sensor comprising:
a first substrate having a proximal end and a distal end;
a second substrate having a proximal end and a distal end;
at least four spacers positioned between the first substrate and the second substrate; wherein the at least four-spacers are positioned in a single plane;
the first substrate, the second substrate, and the at least four-spacers together define a sample chamber; and
the at least four-spacers are positioned such that at least four-sample fill areas are provided through which the sample chamber can be simultaneously filled with a sample.

2. The analyte sensor of claim 1, wherein the sample chamber comprises a perimeter, the perimeter comprising a bounded region defined by the at least four spacers and an unbounded region open to the external environment, and wherein the unbounded region is greater in length than the bounded region.

3. The analyte sensor of claim 1, wherein each of the at least four-spacers is an adhesive material.

4. The analyte sensor of claim 1, wherein the analyte sensor comprises a plurality of electrodes.

5. The analyte sensor of claim 4, wherein one of the plurality of electrodes comprises an analyte-responsive enzyme.

6. The analyte sensor of claim 5, wherein the analyte-responsive enzyme is a glucose-responsive enzyme or a ketone-responsive enzyme.

7. The analyte sensor of claim 1, wherein the sample chamber comprises a sample fill port, and wherein the sample chamber has a volume ($V_c$) in $mm^3$, the sample fill port has an area ($A_p$) in $mm^2$ and $A_p/V_c$ is greater than 0.75 $mm^{-1}$.

8. The analyte sensor of claim 7, wherein $A_p/V_c$ is greater than 1.0 $mm^{-1}$.

9. The analyte sensor of claim 7, wherein $A_p/V_c$ is greater than 1.5 $mm^{-1}$.

10. The analyte sensor of claim 7, wherein $A_p/V_c$ is greater than 2.0 $mm^{-1}$.

11. The analyte sensor of claim 7, wherein $A_p/V_c$ is greater than 2.5 $mm^{-1}$.

12. The analyte sensor of claim 7, wherein $A_p/V_c$ is greater than 3.0 $mm^{-1}$.

13. The analyte sensor of claim 7, wherein $V_c$ is less than 0.10 $mm^3$.

14. The analyte sensor of claim 7, wherein $V_c$ is less than 0.075 $mm^3$.

15. The analyte sensor of claim 7, wherein $V_c$ is less than 0.050 $mm^3$.

16. The analyte sensor of claim 1, wherein two of the at least four-spacers are positioned between the proximal end of the first substrate and the proximal end of the second substrate.

17. The analyte sensor of claim 1, wherein three of the at least four spacers are positioned between the proximal end of the first substrate and the proximal end of the second substrate.

18. The analyte sensor of claim 1, comprising five spacers positioned between the first substrate and the second substrate; wherein the five spacers are positioned in a single plane.

19. The analyte sensor of claim 18, wherein four of the at least five spacers are positioned between the proximal end of the first substrate and the proximal end of the second substrate.

20. The analyte sensor of claim 1, wherein the first substrate comprises a first protrusion positioned at the proximal end of the first substrate, the second substrate comprises a second protrusion positioned at the proximal end of the second substrate, and one of the at least four-spacers is positioned between the first protrusion and the second protrusion and wherein the first substrate comprises a third protrusion positioned at the proximal end of the first substrate, the second substrate comprises a fourth protrusion positioned at the proximal end of the second substrate and another one of the at least four-spacers is positioned between the third protrusion and the fourth protrusion.

* * * * *